United States Patent [19]

Ishikawa et al.

[11] Patent Number: 4,480,103

[45] Date of Patent: Oct. 30, 1984

[54] 4-FLUORO-5-OXYPYRAZOLE DERIVATIVES

[75] Inventors: Nobuo Ishikawa, Yokohama; Tomoya Kitazume, Tokyo, both of Japan

[73] Assignees: Ihara Chemical Industry Co., Ltd., Tokyo; Daikin Kogyo Co., Ltd., Osaka, both of Japan

[21] Appl. No.: 318,366

[22] Filed: Nov. 5, 1981

[30] Foreign Application Priority Data

Nov. 13, 1980 [JP] Japan .................................. 55-160136

[51] Int. Cl.$^3$ .................. C07D 231/16; C07D 231/20; A01N 43/56
[52] U.S. Cl. ...................................... 548/365; 548/116
[58] Field of Search .......................................... 548/365

[56] References Cited

U.S. PATENT DOCUMENTS

| | | | |
|---|---|---|---|
| 3,825,557 | 7/1974 | Hoffmann et al. | 548/116 |
| 4,146,632 | 3/1979 | Hofer et al. | 548/365 |
| 4,163,052 | 7/1979 | Hofer et al. | 424/200 |

OTHER PUBLICATIONS

Al-Hajjar, Chem. Abst. 1978, vol. 88, No. 136,510z.
Kagaruki, S. R. F., et al., "Ring Monofluorinated Hydroxypyrazoles" Bull. Chem. Soc. Jpn., vol. 54, p. 3221-3222 (1981).

*Primary Examiner*—Henry R. Jiles
*Assistant Examiner*—Dale A. Bjorkman
*Attorney, Agent, or Firm*—Oblon, Fisher, Spivak, McClelland & Maier

[57] ABSTRACT

These compounds are especially useful as intermediates to the corresponding thionophosphonic acid esters having insecticidal and acaricidal properties.

4 Claims, No Drawings

4-FLUORO-5-OXYPYRAZOLE DERIVATIVES

BACKGROUND OF THE INVENTION

1. Field of the Invention

The present invention relates to novel 4-fluoro-5-oxypyrazole derivatives which are useful as intermediates for agricultural chemicals and pharmaceutical chemicals.

2. Description of the Prior Art

Organic fluorine compounds have been considered to be important in view of reactivity and biological activity. For example, Futraful, 2-fluorohistidine and Diflubenzuron have been developed as pharmaceutical and agricultural chemicals.

SUMMARY OF THE INVENTION

It is an object of the present invention to provide novel 4-fluoro-5-oxypyrazole derivatives which are useful as pharmaceutical and agricultural chemicals.

The foregoing and other objects of the present invention have been attained by providing 4-fluoro-5-oxypyrazole derivatives having the formula

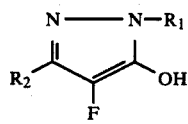
(I)

wherein $R_1$ represents hydrogen atom or a lower alkyl group; and $R_2$ represents a lower alkyl or phenyl group or a phenyl group having one or more substituent of fluorine or chlorine atom or a lower alkyl group or dimethylamino group.

DETAILED DESCRIPTION OF THE PREFERRED EMBODIMENTS

The compounds having the formula (I) are novel compounds and are remarkably useful as intermediates for pharmaceutical or agricultural chemicals.

The typical novel 4-fluoro-5-oxypyrazole derivatives of the present invention include:
(1) 3-phenyl-4-fluoro-5-oxypyrazole;
(2) 1-methyl-3-phenyl-4-fluoro-5-oxypyrazole;
(3) 1-methyl-3-(4-methylphenyl)-4-fluoro-5-oxypyrazole;
(4) 1-methyl-3-(4-chlorophenyl)-4-fluoro-5-oxypyrazole;
(5) 1-methyl-3-(4-dimethylaminophenyl)-4-fluoro-5-oxypyrazole;
(6) 1-methyl-3-(4-fluorophenyl)-4-fluoro-5-oxypyrazole;
(7) 1-methyl-3-(3-methylphenyl)-4-fluoro-5-oxypyrazole;
(8) 3-(4-methylphenyl)-4-fluoro-5-oxypyrazole;
(9) 3-(4-chlorophenyl)-4-fluoro-5-oxypyrazole;
(10) 3-methyl-4-fluoro-5-oxypyrazole;
(11) 1,3-dimethyl-4-fluoro-5-oxypyrazole;
(12) 3-propyl-4-fluoro-5-oxypyrazole; and
(13) 1-methyl-3-propyl-4-fluoro-5-oxypyrazole.

The 4-fluoro-5-oxypyrazole derivatives having the formula (I) can be produced by reacting methyl hydrazine or hydrazine hydrate with an α-fluoro-β-ketoester having the formula

wherein $R_3$ represents a lower alkyl group and $R_2$ is defined above. The reaction is advantageously performed in an alcohol while refluxing.

The present invention will be illustrated by certain examples of the production of the compounds having the formula (I)

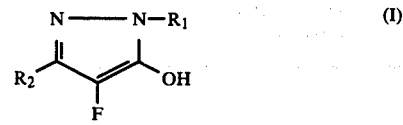
(I)

which are provided for purposes of illustration only and are not intended to be limiting the invention.

EXAMPLE 1

Hydrazine hydrate (0.5 g, 10 mmol) was dissolved into 2 ml of ethanol and the solution was charged into 3 ml of ethanol solution of methyl α-benzoyl-α-fluoroacetate (2.0 g, 10 mmol). The mixture was refluxed while stirring for 3 hours, and then, the reaction mixture was cooled to room temperature. The precipitated dark colored crystals were separated by a filtration. The resulting crude crystals were recrystallized from water-ethanol after a treatment with a decolorizing carbon to obtain 3-phenyl-4-fluoro-5-oxypyrazole having melting point of 184°–186° C. (yield: 61%).

The structure of the compound was confirmed by IR spectrum, NMR spectrum and elemental analysis.

EXAMPLES 2 TO 13

In accordance with the process of Example 1 except using methyl hydrazine instead of hydrazine hydrate (some cases) and using the other α-fluoro-β-ketoester instead of methyl α-benzoyl-α-fluoroacetate (some cases), each reaction was carried out to obtain 4-fluoro-5-oxypyrazole derivatives shown in Table 1 were obtained. The conditions of the reactions and the results are shown in Table 1.

TABLE 1

| Exp. | α-Fluoro-β-ketoester | Hydrazine | Reaction time (hour) | Product 4-Fluoro-5-oxypyrazole derivative | Yield (%) | Physical property mp. (°C.) |
|---|---|---|---|---|---|---|
| 2 | methyl α-benzoyl-α-fluoroacetate | methyl hydrazine | 2 | 1-methyl-3-phenyl-4-fluoro-5-oxypyrazole | 65 | 130–132 |
| 3 | methyl α-(4-methylbenzoyl)-α-fluoroacetate | methyl hydrazine | 3 | 1-methyl-3-(4-methylphenyl)-4-fluoro-5-oxypyrazole | 80 | 200–202 |
| 4 | methyl α-(4-chlorobenzoyl)-α-fluoroacetate | methyl hydrazine | 3 | 1-methyl-3-(4-chlorophenyl)-4-fluoro-5-oxypyrazole | 79 | 229–230 |
| 5 | methyl α-(4-dimethyl- | methyl | 3 | 1-methyl-3-(4-dimethyl- | 58 | 250–252 |

TABLE 1-continued

| Exp. | α-Fluoro-β-ketoester | Hydrazine | Reaction time (hour) | Product 4-Fluoro-5-oxypyrazole derivative | Yield (%) | Physical property mp. (°C.) |
|---|---|---|---|---|---|---|
| | aminobenzoyl)-α-fluoroacetate | hydrazine | | aminophenyl)-4-fluoro-5-oxypyrazole | | |
| 6 | methyl α-(4-fluorobenzoyl)-α-fluoroacetate | methyl hydrazine | 1 | 1-methyl-3-(4-fluorophenyl)-4-fluoro-5-oxypyrazole | 85 | 234–235 |
| 7 | methyl α-(3-methylbenzoyl)-α-fluoroacetate | methyl hydrazine | 1 | 1-methyl-3-(3-methylphenyl)-4-fluoro-5-oxypyrazole | 52 | 220–221 |
| 8 | methyl α-(4-methylbenzoyl)-α-fluoroacetate | hydrazine hydrate | 0.5 | 3-(4-methylphenyl)-4-fluoro-5-oxypyrazole | 98 | 205–206 |
| 9 | methyl α-(4-chlorobenzoyl)-α-fluoroacetate | hydrazine hydrate | 0.5 | 3-(4-chlorophenyl)-4-fluoro-5-oxypyrazole | 94 | 230–233 |
| 10 | ethyl α-acetyl-α-fluoroacetate | hydrazine hydrate | 3 | 3-methyl-4-fluoro-5-oxypyrazole | 52 | 104–106 |
| 11 | ethyl α-acetyl-α-fluoroacetate | methyl hydrazine | 3 | 1,3-dimethyl-4-fluoro-5-oxypyrazole | 56 | 101–103 |
| 12 | ethyl α-butyryl-α-fluoroacetate | hydrazine hydrate | 3 | 3-propyl-4-fluoro-5-oxypyrazole | 53 | 126–128 |
| 13 | ethyl α-butyryl-α-fluoroacetate | methyl hydrazine | 3 | 1-methyl-3-propyl-4-fluoro-5-oxypyrazole | 58 | 123–125 |

4-Fluoro-5-oxypyrazole derivative of the present invention can be used for producing effective insecticides; 4-fluoro-pyrazole derivative having the formula

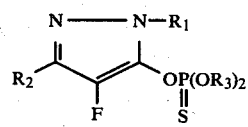

($R_3$ is a lower alkyl group) by reacting it with a compound having the formula

We claim:

1. 4-Fluoro-5-oxypyrazole derivative having the formula

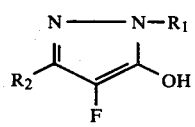

wherein $R_1$ represents hydrogen or a lower alkyl group; and $R_2$ represents a phenyl group, or a phenyl group having one or more substituents selected from fluorine, chlorine, a lower alkyl group and a dimethylamino group.

2. 4-Fluoro-5-oxypyrazole derivative according to claim 1 which is selected from
(1) 3-phenyl-4-fluoro-5-oxypyrazole;
(2) 1-methyl-3-phenyl-4-fluoro-5-oxypyrazole;
(3) 1-methyl-3-(4-methylphenyl)-4-fluoro-5-oxypyrazole;
(4) 1-methyl-3-(4-chlorophenyl)-4-fluoro-5-oxypyrazole;
(5) 1-methyl-3-(4-dimethylaminophenyl)-4-fluoro-5-oxypyrazole;
(6) 1-methyl-3-(4-fluorophenyl)-4-fluoro-5-oxypyrazole;
(7) 1-methyl-3-(3-methylphenyl)-4-fluoro-5-oxypyrazole;
(8) 3-(4-methylphenyl)-4-fluoro-5-oxypyrazole; and
(9) 3-(4-chlorophenyl)-4-fluoro-5-oxypyrazole.

3. 4-Fluoro-5-oxypyrazole derivative having the formula

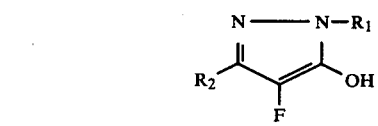

wherein $R_1$ represents a lower alkyl group; and $R_2$ represents a phenyl group, or a phenyl group having one or more substituents selected from fluorine, chlorine, a lower alkyl group and a dimethylamino group.

4. 4-Fluoro-5-oxypyrazole derivative according to claim 3 which is selected from
(1) 1-methyl-3-phenyl-4-fluoro-5-oxypyrazole;
(2) 1-methyl-3-(4-methylphenyl)-4-fluoro-5-oxypyrazole;
(3) 1-methyl-3-(4-chlorophenyl)-4-fluoro-5-oxypyrazole;
(4) 1-methyl-3-(4-dimethylaminophenyl)-4-fluoro-5-oxypyrazole;
(5) 1-methyl-3-(4-fluorophenyl)-4-fluoro-5-oxypyrazole; and
(6) 1-methyl-3-(3-methylphenyl)-4-fluoro-5-oxypyrazole.

* * * * *